United States Patent [19]

Kornis et al.

[11] 4,084,955

[45] Apr. 18, 1978

[54] ORGANIC COMPOUNDS AND PROCESS

[75] Inventors: Gabriel Kornis; Eldon G. Nidy; Henry J. Vostral, all of Kalamazoo, Mich.; Arnolds Steinhards, deceased late of Kalamazoo, Mich., by John J. Killinger

[73] Assignee: The Upjohn Company, Kalamazoo, Mich.

[21] Appl. No.: 681,239

[22] Filed: Apr. 28, 1976

Related U.S. Application Data

[63] Continuation of Ser. No. 316,902, Dec. 20, 1972, abandoned, which is a continuation-in-part of Ser. No. 12,871, Feb. 19, 1970, abandoned.

[51] Int. Cl.$^2$ .................... A01N 9/22; C07D 231/14
[52] U.S. Cl. ........................... 71/92; 71/67; 71/76; 71/88; 71/90; 71/DIG. 1; 260/239 E; 260/239 A; 260/239 B; 260/239 BF; 260/250 B; 260/268 C; 260/293.59; 260/326.8; 544/140; 544/60; 548/376
[58] Field of Search .................... 71/92; 260/310 R

[56] References Cited

U.S. PATENT DOCUMENTS

| | | | |
|---|---|---|---|
| 3,150,148 | 9/1964 | Dulin et al. | 260/310 R |
| 3,303,200 | 2/1967 | Wolf et al. | 260/310 R |
| 3,423,420 | 1/1969 | Buchel et al. | 71/92 |
| 3,446,613 | 5/1969 | Berliner et al. | 71/113 |
| 3,504,008 | 3/1970 | Neighbors | 71/113 |
| 3,625,953 | 12/1971 | Rutz et al. | 71/92 |
| 3,810,911 | 5/1974 | Hoffmann et al. | 260/310 R |
| 3,855,236 | 12/1974 | Kornis et al. | 71/92 |
| 3,957,480 | 5/1976 | Kornis | 71/92 |

OTHER PUBLICATIONS

Giles et al., "Some Iodinated Pyrazole Derivatives," (1966), J. Chem. Soc., pp. 1179–1184, (1966).
Vinokurov et al., "I.R. Spectra of 4-Acylpyrazoles etc.," (1963), CA59, pp. 1615–1616, (1963).
Michaelis et al., "1-Acid Derivatives of 3-Methyl, etc.," (1910), CA4, pp. 2827–2828, (1910).
Habraken et al., "Pyrazoles II. Ionization Constants, etc.," (1966), CA66, No. 85355e., (1967).

*Primary Examiner*—Glennon H. Hollrah
*Attorney, Agent, or Firm*—J. J. Killinger; S. B. Williams, Jr.

[57] ABSTRACT

Certain new 1-(substituted-hydrocarbyl)-di- and trihalopyrazoles have been synthesized. They possess herbicidal and plant growth regulatory activity. The hydrocarbyl group, i.e., alkylene or alkenylene group at the 1-nitrogen of the pyrazole nucleus has either a carboxyl group, an hydroxymethyl group, an hydroxymethyl lower-alkanoate group, a carboxylic lower-alkyl ester group, a cyano group, or a carboxylic amide group. The new compounds are prepared and isolated by conventional chemical reactions and procedures. An improved reaction for making the new carboxylic acids is described. Weed control methods and compositions for herbicidal use are also described.

36 Claims, No Drawings

ORGANIC COMPOUNDS AND PROCESS

This application is a continuation of application Ser. No. 316,902, filed Dec. 20, 1972, now abandoned, which in turn was a continuation-in-part of application Ser. No. 12,871, filed Feb. 19, 1970, now abandoned.

SUMMARY OF THE INVENTION

This invention pertains to new organic compounds, to a process for preparing the same, to a new method for controlling weeds and to new herbicidal compositions. The invention is more particularly directed to new 1-(substituted-hydrocarbyl)-di and trihalopyrazoles; to a new process for preparing the same, particularly lower-alkyl di- and trihalopyrazole-1-alkanoic acids and -1-alkenoic acids; to a new method of controlling weeds with the 1-(substituted-hydrocarbyl)-di- and trihalopyrazoles of this invention; and to new herbicidal compositions containing the same.

The new 1-(substituted-hydrocarbyl)-di- and trihalopyrazoles of this invention have the general structural formula:

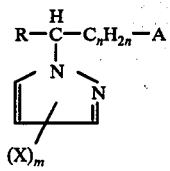

wherein "$n$" is in integer 0, 1, 2, or 3; "X" is a halogen atom; "$m$" is the integer 2 or 3, the halogen atoms being selected independently; "R" is hydrogen, alkyl of from 1 to 10 carbon atoms, inclusive, or alkenyl of from 2 to 10 carbon atoms, inclusive, the sum of the carbon atoms in the group

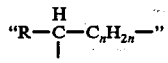

being not more than 11; and "A" is the carboxyl group, the hydroxymethyl group, an hydroxymethyl lower-alkanoate group in which the lower-alkyl moiety is of from 1 to 8 carbon atoms, inclusive, a carboxylic lower-alkyl ester group wherein "lower-alkyl" is of from 1 to 8 carbon atoms, inclusive, the cyano group, or a carboxylic amide group of the formula

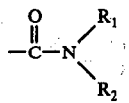

wherein $R_1$ and $R_2$ are hydrogen atoms or independent substituent groups more fully described as follows:

Individually, $R_1$ and $R_2$ are lower-alkyl of from 1 to 8 carbon atoms, inclusive; alkenyl of from 3 to 8 carbon atoms, inclusive; alkynyl of from 3 to 8 carbon atoms, inclusive; aralkyl of from 7 to 13 carbon atoms, inclusive; aryl of from 6 to 10 carbon atoms, inclusive (provided both $R_1$ and $R_2$ are not aryl at the same time); cycloalkyl of from 3 to 8 carbon atoms, inclusive; cycloalkenyl of from 4 to 8 carbon atoms, inclusive; and Collectively, the

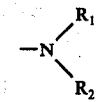

group is a saturated heterocyclic amino group of from 3 to 7 ring atoms, inclusive, having a total of not more than 15 carbon atoms.

DETAILED DESCRIPTION OF THE INVENTION

The foregoing general structural formula and definition of variables provide a broad outline of the scope of this invention. This scope can be more readily recognized by consideration of some specific variations. Accordingly, some specific lower-alkyl groups "of from 1 to 8 carbon atoms, inclusive," are for example: methyl, ethyl, propyl, butyl, pentyl, hexyl, heptyl, octyl, and isomeric forms thereof. Alkyl groups "of from 1 to 10 carbon atoms, inclusive," are those already given, and also nonyl, decyl, and isomeric forms thereof.

Some specific alkenyl groups "of from 3 to 8 carbon atoms, inclusive," are for example: allyl, 1-methylallyl, 2-methylallyl (methallyl), 2-butenyl (crotyl), 3-butenyl, 1,2-dimethylallyl, 3-methyl-2-butenyl, 3-pentenyl, 2,3-dimethyl-2-butenyl, 1,1,2-trimethylallyl, 1,3-dimethyl-2-butenyl, 1-ethyl-2-butenyl, 4-methyl-2-pentenyl, 2-ethyl-2-pentenyl, 4,4-dimethyl-2-pentenyl, 2-heptenyl, 2-octenyl, 5-octenyl, 1,4-dimethyl-4-hexenyl, and the like. Alkenyl groups "of from 2 to 10 carbon atoms, inclusive," are those already given, and also vinyl, 2-nonenyl, 2-decenyl, and the like.

Some specific alkynyl groups "of from 3 to 8 carbon atoms, inclusive," are 2-propynyl, 3-butynyl, 2-pentynyl, 1,1-dimethyl-2-propynyl, 2-hexynyl, 2-heptynyl, 2-octynyl, 1,1,3-trimethyl-4-pentynyl, and the like.

Some specific aralkyl groups "of from 7 to 13 carbon atoms, inclusive," are for example: benzyl, phenethyl, 1-phenylethyl, 2-phenylpropyl, 4-phenylbutyl, 6-phenylhexyl, 5-phenyl-2-methylpentyl, benzhydryl, 1-naphthylmethyl, 2-(1-naphthyl)ethyl, 2-(2-naphthyl)ethyl, and the like.

The phrase "aryl of from 6 to 10 carbon atoms, inclusive," includes for example, phenyl, the tolyls, the xylyls, mesityl, 4-tert-butylphenyl, 2,5-dichlorophenyl, 3-anisyl, 4-ethylphenyl, 3,4,5-trimethoxyphenyl, 4-bromo-2-methoxyphenyl, 2-chloro-4-tolyl, and the like.

The phrase "cycloalkyl of from 3 to 8 carbon atoms, inclusive," includes for example, cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-trimethylcyclobutyl, cyclopentyl, 2,2-dimethylcyclopentyl, cyclohexyl, 3-methylcyclohexyl, 2,2-dimethylcyclohexyl, cycloheptyl, cyclooctyl, and the like.

Cycloalkenyl groups "of from 4 to 8 carbon atoms, inclusive," are for example: 2-cyclobutenyl, 3-cyclopentenyl, 3-cyclohexenyl, 2-ethyl-3-cyclohexenyl, and the like.

The phrase "saturated heterocyclic amino group of from 3 to 7 ring atoms, inclusive, having a total of not more than 15 carbon atoms," includes for example, aziridinyl, lower-alkylaziridinyl, for example, 2-methylaziridinyl, 2-ethylaziridinyl, and 2-butylaziridinyl, polylower-alkyl aziridinyl, for example, 2,3-dimethylaziridinyl and 2,2-dimethylaziridinyl, azetidinyl, lower-alkylazetidinyl, for example, 2-methylazetidinyl, 3-methylazetidinyl, and 2-octylazetidinyl, polyloweralkylazetidinyl, for example, 2,2-dimethylazetidinyl, 3,3-diethylazetidinyl, 2,4,4-trimethylazetidinyl, and 2,3,4-trimethylazetidinyl, pyrrolidinyl, lower-alkylpyrrolidinyl, for example, 2-methylpyrrolidinyl, 3-butylpyrrolidinyl, and 2-isohexylpyrrolidinyl, polyloweralkylpyrrolidinyl, for example, 2,3-dimethylpyrrolidinyl, 2,2-dimethylpyrrolidinyl, 2,5-diethylpyrrolidinyl, and 2,3,5-trimethylpyrrolidinyl, piperidino, lower-alkylpiperidino, for example, 2-methylpiperidino, 3-methylpiperidino, 4-methylpiperidino, 3-isopropylpiperidino, and 4-tert-butylpiperidino, polylower-alkylpiperidino, for example, 3,4-diethylpiperidino, 2-methyl-5-ethylpiperidino, 3,5-dipentylpiperidino, 2,4,6-trimethylpiperidino, and 2,3,5-triethylpiperidino, hexamethyleneimino, lower-alkylhexamethyleneimino, for example, 2-ethylhexamethyleneimino, 4-tert-butylhexamethyleneimino, and 3-heptylhexamethyleneimino, polylower-alkylhexamethyleneimino, for example, 2,4-dimethylhexamethyleneimino, 3,3-dimethylhexamethyleneimino, 2,4,6-tripropylhexamethyleneimino, and 2,2-dibutylhexamethyleneimino, 4-lower-alkylpiperazinyl, for example, 4-methylpiperazinyl and 4-isopropylpiperazinyl, polylower-alkylpiperazinyl, for example, 2,2,4,5,5-pentamethylpiperazinyl and 2,4,5-trimethylpiperazinyl, morpholino, lower-alkylmorpholino, for example 2-ethylmorpholino and 3-isobutylmorpholino, polylower-alkylmorpholino, for example, 2-ethyl-5-methylmorpholino, 3,3-dimethylmorpholino, and 2,6-di-tert-butylmorpholino, thiamorpholino, lower-alkylthiamorpholino, for example, 3-methylthiamorpholino, and polylower-alkylthiamorpholino, for example, 2,3,6-trimethylthiamorpholino and 2,3,5,6-tetramethylthiamorpholino.

The foregoing specified and many other like saturated heterocyclic amino groups are contemplated as being within the scope of this invention. It will be noted that the saturated amino heterocycle can be other than alkyleneamino and there can be a second hetero atom in the ring, i.e., an oxygen atom, a sulfur atom, or a second nitrogen atom as a ring member. In general, the second hetero atom is preferably in the 4-position of a six-membered ring, but it can be in the 3-position. Accordingly, referring to the phrase "Collectively the

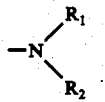

group is a saturated heterocyclic amino group of from 3 to 7 atoms, inclusive," it will be recognized that the $R_1$ and $R_2$ chain can be alkylene, oxadialkylene, e.g.,

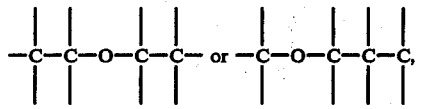

thiadialkylene, e.g.,

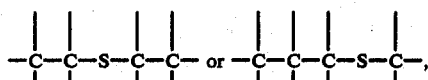

or N-alkylazadialkylene, e.g.,

-continued

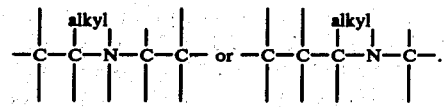

Accordingly, a further definition of the phrase is:
Collectively, $R_1$ and $R_2$ taken as a unit with the N< atom, are saturated heterocyclic amino groups of from 3 to 7 ring atoms, inclusive, each group having a total of not more than 15 carbon atoms, one of the ring atoms being selected from carbon, oxygen, sulfur, or a second nitrogen atom, the other ring atoms being carbon, so that $R_1$-$R_2$ as a unit, is alkylene, oxadialkylene, thiadialkylene, or N-alkylazadialkylene, respectively.

The new 1-(substituted-hydrocarbyl)-di- and trihalopyrazoles of Formula I are prepared by conventional chemical reactions. The new di- and trihalopyrazole-1-alkanoamides and 1-alkanoamides (compounds according to Formula I wherein "A" is a carboxylic amide group) are prepared in accordance with conventional methods for preparing carboxylic acid amides. This class of compounds in accordance with the invention has the structural formula:

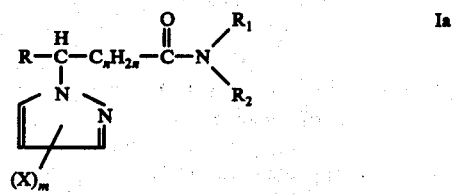

wherein n, X, m, R, $R_1$ and $R_2$ are as previously defined.

Illustratively, unsubstituted amides (compounds of Formula Ia wherein $R_1$ and $R_2$ are both hydrogen) are prepared by reacting an alkyl di- or trihalopyrazole-1-alkanoate or -1-alkenoate, or a di- or trihalopyrazole-1-alkanoic or -1-alkenoic acid chloride with ammonia. For example, a solution of an alkyl di- or trihalopyrazole-1-alkanoate or -1-alkenoate in an organic solvent medium, preferably an alkanol, e.g., ethanol, is saturated with ammonia and the reaction mixture is set aside at about 25° C. for several days or until the reaction is completed. Alternatively, the reaction mixture can be heated in order to speed up the reaction, care being taken to avoid loss of ammonia or by replenishing it. The di- or trihalopyrazole-1-alkanoamide or -1-alkenoamide thus produced is recovered by removing the solvent and excess ammonia. It can be purified by conventional methods, e.g., distillation, column chromatography, and recrystallization.

Further illustratively, N-substituted amides (compounds of Formula Ia wherein $R_1$ and $R_2$ or one of them is one of the defined substituent groups) are prepared after first preparing a di- or trihalopyrazole-1-alkanoic or -1-alkenoic acid halide, e.g., a chloride or bromide, and then reacting it with a primary or secondary amine. Di- or trihalopyrazole-1-alkanoic and -1-alkenoic acid chlorides, for example, are readily prepared by heating a di- or trihalopyrazole-1-alkanoic or -1-alkenoic acid with thionyl chloride. The desired amide is then prepared by slowly adding the acid chloride to a solution of the selected amine and optionally heating the reaction mixture after the addition is made in order to complete the reaction.

A strongly basic acid acceptor such as a tertiary amine, illustratively a trialkylamine, e.g., triethylamine, can be included in the reaction mixture if efficient reaction of the selected primary or secondary amine is desired. Solvents suitable for this latter reaction include benzene, toluene, diethyl ether, and tetrahydrofuran. The desired N-substituted-di- or trihalopyrazole-1-alkanoamide or -1-alkenoamide is recovered by washing out with water the amine hydrochloride formed during the reaction and removing the solvent. The desired product can be purified by recrysallization.

When lower-boiling amines are employed in the foregoing reaction and the reaction mixture is heated, loss of amine from the reaction mixture can be prevented by using a chilled condenser or by carrying out the reaction in a closed system.

The new alkyl di- and trihalopyrazole-1-alkanoate and -1-alkenoate esters of this invention according to Formula I have the structural formula:

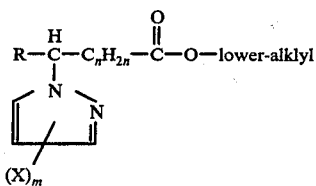

Ib wherein $n$, X, $m$, R, and lower-alkyl are as previously defined. Compounds according to Formula Ib are prepared by reacting an alkali metal salt (preferably a sodium or potassium salt) of a di- or trihalopyrazole with an alkyl haloalkanoate or haloalkenoate. A representative formula of suitable alkyl haloalkanoates and haloalkenoates is as follows:

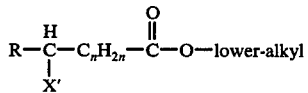

II wherein $n$, R and lower-alkyl are as previously defined and X' is halogen, e.g., chlorine, bromine, or iodine.

The alkali metal salt of the trihalopyrazole is prepared, preferably in situ, by mixing an alkali metal, an alkali metal alkoxide, or an alkali metal hydride, with a solution of the trihalopyrazole in an organic solvent medium. To the solution of alkali metal trihalopyrazole thus obtained is then added, slowly, a selected alkyl haloalkanoate or haloalkenoate according to Formula II. After the reaction is completed, the reaction mixture can be concentrated, acidified, and then made weakly basic with an alkali metal carbonate. The desired alkyl di- or trihalopyrazole-1-alkanoate or -1-alkenoate ester is recovered and purified by conventional methods such as solvent extraction, solvent evaporation, precipitation, and recrystallization.

The new di- and trihalopyrazole-1-alkanoic and -1-alkenoic acids of Formula I (compounds wherein "A" is carboxyl) are prepared from the corresponding esters by conventional alkaline hydrolysis. If desired, the alkyl di- or trihalopyrazole-1-alkanoate or -1-alkenoate is hydrolyzed with an alkali metal hydroxide in the reaction mixture in which it is formed, and the alkanoic or alkenoic acid is recovered by adding strong acid to neutralize the base and to precipitate the di- or trihalopyrazole-1-alkanoic or -1-alkenoic acid.

In accordance with a preferred new process of this invention, the di- and trihalopyrazole-1-alkanoic and -1-alkenoic acids are prepared by first reacting a di- or trihalopyrazole with an alkyl haloalkanoate or haloalkenoate (according to Formula II) in the presence of an alkali metal carbonate such as potassium carbonate or sodium carbonate and acetone, and then hydrolyzing the thus-produced ester to the corresponding acid.

The di- or trihalopyrazole is dissolved in acetone and a solid anhydrous alkali metal carbonate is added. The mixture is heated for a few minutes, then cooled, and the alkyl haloalkanoate or haloalkenoate is added. After further heating at the reflux temperature and cooling, aqueous alkali metal hydroxide is added, the acetone is removed and the reaction mixture is reheated to the reflux temperature to effect hydrolysis. The solution that results containing di- or trihalopyrazole-1-alkanoic or -1-alkenoic acid alkali metal salt is acidified to precipitate the free acid. The free acid is collected on a filter, washed free of salts, and dried.

The new di- or trihalopyrazole-1-alkanoic and -1-alkenoic acids forms salts with alkali metals, alkaline earth metals, ammonia, and amines. Salts are prepared by neutralizing the acid with an alkali metal hydroxide such as sodium, potassium or lithium hydroxide, with an alkaline earth metal hydroxide such as calcium, barium or magnesium hydroxide, with ammonia or with an amine, e.g., mono-, di-, and triethanolamine, triethylamine, isopropanolamine, isopropylamine, piperidine, and morpholine. Oil-soluble salts are obtained by using tertiary-alkyl primary amines wherein the amino nitrogen is attached to a tertiary carbon and the tertiary-alkyl group is of from about 12 to about 22 carbon atoms, inclusive.

3,4-Dihalopyrazole-1-alkanols and -1-alkenols of Formula I (compounds wherein "A" is hydroxymethyl) are conveniently obtained from esters of Formula Ib by reduction with lithium aluminum hydride in an inert organic solvent such as diethyl ether, although other methods known to those skilled in the art for reducing esters to alcohols can be used. If a trihalo ester (compound of Formula Ib in which $m$ is 3) is thus reduced, the halogen atom in the 5-position is replaced by a hydrogen atom.

3,4,5-Trihalopyrazole-1-alkanols and -1-alkenols of Formula I (compounds wherein "A" is hydroxymethyl) are advantageously prepared in accordance with the procedure illustrated in Examples 40 and 41. In this procedure a di- or trihalopyrazole is reacted with a haloalkyl or haloalkenyl alkanoate to obtain a lower-alkanoate ester of a di- or trihalopyrazole-1-alkanol or -1-alkenol (e.g., see Example 40), which if desired can be hydrolyzed to obtain a di- or trihalopyrazole-1-alkanol or -1-alkenol (e.g., see Example 41).

The new di- and trihalopyrazole-1-alkanonitriles and -1-alkenonitriles according to Formula I are prepared by mixing and heating an alkali metal salt of a di- or trihalopyrazole with a chloro- or bromoalkanonitrile or -alkenonitrile in an inert organic solvent such as toluene or benzene. The thus prepared di- or trihalopyrazole-1-alkanonitrile or -1-alkenonitrile is recovered by washing out the salt formed by the reaction and any by-products of the reaction, drying the organic phase and removing the solvent. The nitriles can be purified by conventional recrystallization.

The new di- and trihalopyrazole-1-alkanonitriles and -1-alkenonitriles according to Formula I are also prepared from N-unsubstituted-di- and trihalopyrazole-1-alkanoamides and -1-alkenoamides by heating the amide with phosphorus pentoxide or phosphorus oxychloride as described in Organic Syntheses, Coll. Vol. 3, p. 493 (1955). The desired di- or trihalopyrazole-1-alkanonitrile or -1-alkenonitrile is recovered by distillation or solvent extraction and precipitation.

EXAMPLE 1

Preparation of Ethyl 3,4,5-Tribromopyrazole-1-acetate

A quantity (92 gm., 0.3 mole) 3,4,5-tribromopyrazole was added with vigorous stirring to a solution of 7.1 gm. sodium (0.31 mole) in 300 ml. absolute ethanol. After the mixing was complete, 100 gm. (0.6 mole) ethyl bromoacetate was added dropwise while stirring was continued. The mixture was diluted with 200 ml. absolute ethanol and this reaction mixture was stirred at about 25° C. for about 18 hrs. After removing most of the ethanol by evaporation under reduced pressure, 100 ml. of 6 N hydrochloric acid was added to the residue, and this aqueous acid mixture was made alkaline with solid sodium carbonate. The aqueous layer was separated and extracted with three 60-ml. portions of ether. The ether extracts were combined, washed with three 40-ml. portions of water, and dried with anhydrous magnesium sulfate. After removing the ether by evaporation under reduced pressure, there was obtained a white solid. Recrystallization from technical hexane (Skellysolve B, a mixture of isomeric hexanes having a boiling range between 61° C. and 69° C.) gave 96.0 gm. of ethyl 3,4,5-tribromopyrazole-1-acetate having a melting point at 101° to 103° C.

Analysis: Calc'd. for $C_7H_7Br_3N_2O_2$: C, 21.51; H, 1.81; N, 7.17; Br, 61.33. Found: C, 21.79; H, 1.62; N, 6.96; Br, 61.56.

Following the same procedure, but substituting methyl 2-bromopropionate, ethyl 3-bromopropionate, ethyl 4-bromobutyrate, isopropyl bromoacetate, tert-butyl bromoacetate, pentyl bromoacetate, octyl 2-bromopropionate, ethyl 2-bromohexanoate, ethyl 2-bromooctanoate, ethyl 2-bromodecanoate, ethyl 2-bromododecanoate, ethyl 2-bromo-4-methylpentanoate and ethyl 2-bromo-9-dodecylenate for ethyl bromoacetate, there are prepared: methyl 3,4,5-tribromo-α-methylpyrazole-1-acetate, ethyl 3,4,5-tribromopyrazole-1-propionate, ethyl 3,4,5-tribromopyrazole-1-butyrate, isopropyl 3,4,5-tribromopyrazole-1-acetate, tert-butyl 3,4,5-tribromopyrazole-1-acetate, pentyl 3,4,5-tribromopyrazole-1-acetate, octyl 3,4,5-tribromo-α-methylpyrazole-1-acetate, ethyl 3,4,5-tribromo-α-butylpyrazole-1-acetate, ethyl 3,4,5-tribromo-α-hexylpyrazole-1-acetate, ethyl 3,4,5-tribromo-α-octylpyrazole-1-acetate, ethyl 3,4,5-tribromo-α-decylpyrazole-1-acetate, ethyl 3,4,5-tribromo-α-isobutylpyrazole-1-acetate, and ethyl 3,4,5-tribromo-α-(7-decenyl)pyrazole-1-acetate, respectively.

EXAMPLE 2

Preparation of 3,4,5-Tribromopyrazole-1-propionic Acid

A mixture consisting of 9.1 gm. (0.03 mole) 3,4,5-tribromopyrazole and 8.1 gm. (0.045 mole) ethyl 3-bromopropionate was heated at 140° C. for 24 hrs. in an atmosphere of nitrogen. After cooling, 80 ml. 0.5 N aqueous sodium hydroxide was added to the reaction mixture and it was heated at the reflux temperature for 3 hrs. After cooling again and adding 1 N aqueous hydrochloric acid until the mixture was pH 2, a precipitate formed. The precipitate was collected on a filter and recrystallized from a mixture of ether and technical hexane. There was thus obtained 10.1 gm. of 3,4,5-tribromopyrazole-1-propionic acid having a melting point at 112° to 113° C.

Analysis: Calc'd. for $C_6H_5Br_3N_2O_2$: C, 19.12; H, 1.33; N, 7.43; Br, 63.61. Found: C, 19.31; H, 1.54; N, 7.44; Br, 64.05.

Following the same procedure, but substituting 3,5-dichloropyrazole, 3,4,5-triiodopyrazole, 3,4-dibromopyrazole, and 3,5-dibromo-4-chloropyrazole for 3,4,5-tribromopyrazole, there are prepared the corresponding: 3,5-dichloropyrazole-1-propionic acid, 3,4,5-triiodopyrazole-1-propionic acid, 3,4-dibromopyrazole-1-propionic acid, and 3,5-dibromo-4-chloropyrazole-1-propionic acid, respectively.

EXAMPLE 3

Preparation of 3,4,5-Tribromopyrazole-1-acetic acid

A suspension of 3.9 gm. (0.01 mole) ethyl 3,4,5-tribromopyrazole-1-acetate (prepared in Example 1) in 20 ml. 0.5 N aqueous sodium hydroxide was heated at the reflux temperature for 2 hrs. The reaction mixture became a clear solution and was cooled. After dilution with 50 ml. water and acidification to pH 2 with 1 N hydrochloric acid, a white precipitate formed. The precipitate was collected on a filter, washed thoroughly with water and recrystallized from a mixture of ethanol and water. There was thus obtained 2.6 gm. 3,4,5-tribromopyrazole-1-acetic acid having a melting point of 212° to 215° C.

Analysis: Calc'd. for $C_5H_3Br_3N_2O_2$: C, 16.55; H, 0.83; N, 7.72; Br, 66.08. Found: C, 16.62; H, 0.89; N, 7.81; Br, 65.88.

By neutralizing the above acid with sodium hydroxide, calcium hydroxide, ammonia, triethylamine and piperidine in an aqueous medium, and then evaporating the reaction mixture under reduced pressure, there are obtained the sodium, calcium, ammonium, triethylammonium and piperidinium salts, respectively, of 3,4,5-tribromopyrazole-1-acetic acid.

EXAMPLE 4

Preparation of Ethyl 3,4,5-Tribromo-α-methylpyrazole-1-Acetate

Following the procedure of Example 1, but substituting ethyl 2-bromopropionate for ethyl bromoacetate, there was prepared ethyl 3,4,5-tribromo-α-methylpyrazole-1-acetate having a melting point at 64° to 66° C.

Analysis: Calc'd. for $C_8H_9Br_3N_2O_2$: C, 23.73; H, 2.24; N, 6.92; Br, 59.21. Found: C, 23.88; H, 2.55; N, 6.98; Br, 59.07.

EXAMPLE 5

Preparation of 3,4,5-Tribromo-α-methylpyrazole-1-acetic acid

Following the procedure of Example 3, but substituting ethyl 3,4,5-tribromo-α-methylpyrazole-1-acetate (prepared in Example 4) for ethyl 3,4,5-tribromopyrazole-1-acetate, there was prepared 3,4,5-tribromo-α-methylpyrazole-1-acetic acid having a melting point at 162° to 163.5° C.

Analysis: Calc'd. for $C_6H_5Br_3N_2O_2$: C, 19.12; H, 1.34; N, 7.43; Br, 63.61. Found: C, 19.27; H, 1.45; N, 7.34; Br, 63.74.

EXAMPLE 6

Preparation of 3,4,5-Tribromopyrazole-1-butyric Acid

Following the procedure of Example 2, but substituting ethyl 4-bromobutyrate for ethyl 3-bromopropionate, there was prepared 3,4,5-tribromopyrazole-1-butyric acid having a melting point at 128.5° to 130° C.

Analysis: Calc'd. for $C_7H_7Br_3N_2O_2$: C, 21.51; H, 1.81; N, 7.17; Br, 61.33. Found: C, 21.98; H, 1.98; N, 7.26; Br, 61.45.

EXAMPLE 7

Following the procedure of Example 2, but substituting ethyl 2-bromo-3-butenoate and ethyl 3-bromo-2-methylpropionate for ethyl 3-bromopropionate, there are prepared:

3,4,5-tribromopyrazole-α-vinyl-1-acetic acid, and 3,4,5-tribromo-α-methylpyrazole-1-propionic acid, respectively.

EXAMPLE 8

Following the procedure of Example 1, but substituting methyl bromoacetate, propyl bromoacetate, butyl bromoacetate, isobutyl bromoacetate, and hexyl bromoacetate for ethyl bromoacetate, there are prepared:
methyl 3,4,5-tribromopyrazole-1-acetate,
propyl 3,4,5-tribromopyrazole-1-acetate,
butyl 3,4,5-tribromopyrazole-1-acetate,
isobutyl 3,4,5-tribromopyrazole-1-acetate, and
hexyl 3,4,5-tribromopyrazole-1- acetate, respectively.

EXAMPLE 9

Preparation of 3,4,5-Tribromopyrazole-1-acetamide

A solution consisting of 9.7 gm. (0.025 mole) ethyl 3,4,5-tribromopyrazole-1-acetate in 250 ml. ethanol was saturated with gaseous ammonia and held at about 25° C. for 3 days. After removing most of the ethanol by evaporation under reduced pressure, the solids that formed were collected on a filter and recrystallized from a mixture of ethanol and water. There was thus obtained 5.8 gm. of 3,4,5-tribromopyrazole-1-acetamide having a melting point at 234° to 236° C.

Analysis: Calc'd. for $C_5H_4Br_3N_3O$: C, 16.60; H, 1.11; N, 11.61; Br, 66.26. Found: C, 16.58; H, 1.15; N, 11.54; Br, 65.59.

EXAMPLE 10

Preparation of 3,4,5-Tribromo-N,N,α-trimethylpyrazole-1-acetamide

A mixture consisting of 70 gm. (0.186 mole) 3,4,5-tribromo-α-methylpyrazole-1-acetic acid and 70 ml. thionyl chloride was heated at the reflux temperature for 3½ hrs. Any excess thionyl chloride was then removed by evaporation under reduced pressure. The thus-obtained 3,4,5-tribromo-α-methylpyrazole-1-acetyl chloride was dissolved in 200 ml. dry benzene, and the solution was added dropwise with stirring to a solution consisting of 70 ml. dimethylamine in 300 ml. dry benzene. After the addition of the acid chloride to the amine was completed, the reaction mixture was stirred at about 25° C. for ½ hr. and then heated at the reflux temperature for another ½ hr. After cooling, the mixture was washed three times with 75-ml. portions of water, and dried over anhydrous sodium sulfate. The benzene was removed by evaporation under reduced pressure and the white solid thus obtained was recrystallized from a mixture of benzene and technical hexane to give 67 gm. of 3,4,5-tribromo-N,N,α-trimethylpyrazole-1-acetamide having a melting point at 130.5° to 132° C.

Analysis: Calc'd. for $C_8H_{10}Br_3N_3O$: C, 23.79; H, 2.50; N, 10.40; Br, 59.35. Found: C, 23.91; H, 2.40; N, 10.43; Br, 59.44.

Following the same procedure but substituting 1,1-dimethyl-2-propynylamine, isopropylamine, diisopropylamine, dibutylamine, dipentylamine, dihexylamine, benzylamine, dicyclohexylamine, 3-cyclopentenylamine, pyrrolidine, piperidine, hexamethyleneimine, and thiamorpholine for dimethylamine, there are prepared the corresponding 3,4,5-tribromo-N-(1,1-dimethyl-2-propynyl)-α-methylpyrazole-1-acetamide, 3,4,5-tribromo-N-isopropyl-α-methylpyrazole-1-acetamide, 3,4,5-tribromo-N,N-diisopropyl-α-methylpyrazole-1-acetamide, 3,4,5-tribromo-N,N-dibutyl-α-methylpyrazole-1-acetamide, 3,4,5-tribromo-N,N-dipentyl-α-methylpyrazole-1-acetamide, 3,4,5-tribromo-N,N-dihexyl-α-methylpyrazole-1-acetamide, 3,4,5-tribromo-N-benzyl-α-methylpyrazole-1-acetamide, 3,4,5-tribromo-N,N-dicyclohexyl-α-methylpyrazole-1-acetamide, 3,4,5-tribromo-N-(3-cyclopentenyl)-α-methylpyrazole-1-acetamide, 3,4,5-tribromo-N,N-(tetramethylene)-α-methylpyrazole-1-acetamide, 3,4,5-tribromo-N,N-(pentamethylene)-α-methylpyrazole-1-acetamide, 3,4,5-tribromo-N,N-(hexamethylene)-α-methylpyrazole-1-acetamide, and 3,4,5-tribromo-N,N-(3-thiapentamethylene)-α-methylpyrazole-1-acetamide, respectively.

EXAMPLE 11

Preparation of 3,4,5-Tribromo-N,α-dimethylpyrazole-1-acetamide

Following the same procedure as Example 10, but substituting methylamine for dimethylamine, there was prepared 3,4,5-tribromo-N,α-dimethylpyrazole-1-acetamide having a melting point at 226° to 227° C.

Analysis: Calc'd. for $C_7H_8Br_3N_3O$: C, 21.56; H, 2.06; N, 10.77; Br, 61.49. Found: C, 21.93; H, 2.01; N, 10.85; Br, 61.39.

EXAMPLE 12

Preparation of 3,4,5-Tribromo-N-methyl-α-ethylpyrazole-1-acetamide

Following the same procedure as Example 10, but substituting 3,4,5-tribromo-α-ethylpyrazole-1-acetic acid for 3,4,5-tribromo-α-methylpyrazole-1-acetic acid and substituting methylamine for dimethylamine, there was prepared 3,4,5-tribromo-N-methyl-α-ethylpyrazole-1-acetamide having a melting point at 178° to 180° C.

Analysis: Calc'd. for $C_8H_{10}Br_3N_3O$: C, 23.79; H, 2.50; N, 10.40; Br, 59.35. Found: C, 23.82; H, 2.56; N, 10.42; Br, 59.64.

EXAMPLE 13

Preparation of 3,4,5-Tribromo-α-methylpyrazole-1-acetamide

Following the same procedure as Example 10, but substituting ammonia for dimethylamine, there was prepared 3,4,5-tribromo-α-methylpyrazole-1-acetamide having a melting point at 188° to 189° C.

Analysis: Calc'd. for $C_6H_6Br_3N_3O$: C, 19.17; H, 1.61; N, 11.17; Br, 63.78. Found: C, 19.38; H, 1.50; N, 11.07; Br, 63.51.

EXAMPLE 14

Preparation of 3,4,5-Tribromo-N,N-dimethyl-α-ethylpyrazole-1-acetamide

Following the procedure of Example 10, but substituting 3,4,5-tribromo-α-ethylpyrazole-1-acetic acid for 3,4,5-tribromo-α-methylpyrazole-1-acetic acid, there was prepared 3,4,5-tribromo-N,N-dimethyl-α-ethylpyrazole-1-acetamide having a melting point at 88.5° to 90.5° C.

Analysis: Calc'd. for $C_9H_{12}Br_3N_3O$: C, 25.86; H, 2.90; N, 10.05; Br, 57.36. Found: C, 26.06; H, 2.96; N, 10.06; Br, 57.56.

EXAMPLE 15

Preparation of 3,4,5-Tribromo-N-ethyl-α-methylpyrazole-1-acetamide

Following the same procedure as Example 10, but substituting ethylamine for dimethylamine, there was prepared 3,4,5-tribromo-N-ethyl-α-methylpyrazole-1-acetamide having a melting point at 211° to 211.5° C.

Analysis: Calc'd. for $C_8H_{10}Br_3N_3O$: C, 23.79; H, 2.50; N, 10.40; Br, 59.35. Found: C, 24.08; H, 2.66; N, 10.22; Br, 59.41.

EXAMPLE 16

Preparation of 3,4,5-Tribromo-N,N-diethyl-α-methylpyrazole-1-acetamide

Following the same procedure as Example 10, but substituting diethylamine for dimethylamine, there was prepared 3,4,5-tribromo-N,N-diethyl-α-methylpyrazole-1-acetamide having a melting point at 69° to 71° C.

Analysis: Calc'd. for $C_{10}H_{14}Br_3N_3O$: C, 27.80; H, 3.26; N, 9.72; Br, 55.50. Found: C, 28.14; H, 3.29; N, 9.74; Br, 55.50.

EXAMPLE 17

Preparation of 3,4,5-Tribromo-N,Nα-triethylpyrazole-1-acetamide

Following the same procedure as Example 10, but substituting 3,4,5-tribromo-α-ethylpyrazole-1-acetic acid for 3,4,5-tribromo-α-methylpyrazole-1-acetic acid and substituting diethylamine for dimethylamine, there was prepared 3,4,5-tribromo-N,Nα-triethylpyrazole-1-acetamide having a melting point at 99° to 101° C.

Analysis: Calc'd. for $C_{11}H_{16}Br_3N_3O$: C, 29.62; H, 3.62; N, 9.42; Br, 53.75. Found: C, 29.78; H, 3.92; N, 9.41; Br, 53.85.

EXAMPLE 18

Preparation of 3,4,5-Tribromo-N,N-dipropyl-α-methylpyrazole-1-acetamide

Following the procedure of Example 10, but substituting dipropylamine for dimethylamine, there was prepared 3,4,5-tribromo-N,N-dipropyl-α-methylpyrazole-1-acetamide having a melting point at 89.5° to 91° C.

Analysis: Calc'd. for $C_{12}H_{18}Br_3N_3O$: C, 31.33; H, 3.94; N, 9.13; Br, 52.12. Found: C, 31.56; H, 3.92; N, 9.16; Br, 52.41.

EXAMPLE 19

Preparation of 3,4,5-Tribromo-N,N-dipropyl-α-ethylpyrazole-1-acetamide

Following the same procedure as Example 10, but substituting dipropylamine for dimethylamine and substituting 3,4,5-tribromo-α-ethylpyrazole-1-acetic acid for 3,4,5-tribromo-α-methylpyrazole-1-acetic acid, there was prepared 3,4,5-tribromo-N,N-dipropyl-α-ethylpyrazole-1-acetamide having a melting point at 66.5° to 68° C.

Analysis: Calc'd. for $C_{13}H_{20}Br_3N_3O$: C, 32.93; H, 4.25; N, 8.86; Br, 50.57. Found: C, 32.85; H, 4.41; N, 8.70; Br, 50.80.

EXAMPLE 20

Preparation of 3,4,5-Tribromo-N,N-dimethylpyrazole-1-acetamide

Following the procedure of Example 10, but substituting 3,4,5-tribromopyrazole-1-acetic acid for 3,4,5-tribromo-α-methylpyrazole-1-acetic acid, there was prepared 3,4,5-tribromo-N,N-dimethylpyrazole-1-acetamide having a melting point at 176.5° to 177.5° C.

Analysis: Calc'd. for $C_7H_8Br_3N_3O$: C, 21.56; H, 2.07; N, 10.78; Br, 61.49. Found: C, 21.74; H, 2.10; N, 10.58; Br, 61.75.

EXAMPLE 21

Preparation of 3,4,5-Tribromo-N-allyl-α-methylpyrazole-1-acetamide

Following the same procedure as Example 10, but substituting allylamine for dimethylamine, there was prepared 3,4,5-tribromo-N-allyl-α-methylpyrazole-1-acetamide having a melting point at 187° to 187.5° C.

Analysis: Calc'd. for $C_9H_{10}Br_3N_3O$: C, 25.99; H, 2.42; N, 10.10; Br, 57.64. Found: C, 26.19; H, 2.43; N, 10.04; Br, 57.63.

EXAMPLE 22

Preparation of 3,4,5-Tribromo-N,N-diallyl-α-methylpyrazole-1-acetamide

Following the same procedure as Example 10, but substituting diallylamine for dimethylamine, there was prepared 3,4,5-tribromo-N,N-diallyl-α-methylpyrazole-1-acetamide having a melting point at 72° to 74° C.

Analysis: Calc'd. for $C_{12}H_{14}Br_3N_3O$: C, 31.61; H, 3.09; N, 9.21; Br, 52.58. Found: C, 31.67; H, 2.97; N, 8.96; Br, 52.75.

EXAMPLE 23

Preparation of 3,4,5-Tribromo-N,N-diallyl-α-ethylpyrazole-1-acetamide

Following the same procedure as Example 10, but substituting 3,4,5-tribromo-α-ethylpyrazole-1-acetic acid for 3,4,5-tribromo-α-methylpyrazole-1-acetic acid and substituting diallylamine for dimethylamine there was prepared 3,4,5-tribromo-N,N-diallyl-α-ethylpyrazole-1-acetamide having a melting point at 72.5° to 74° C.

Analysis: Calc'd. for $C_{13}H_{16}Br_3N_3O$: C, 33.22; H, 3.43; N, 8.94; Br, 51.01. Found: C, 33.22; H, 3.64; N, 8.82; Br, 50.65.

EXAMPLE 24

Preparation of 3,4,5-Tribromo-N-butyl-α-methylpyrazole-1-acetamide

Following the same procedure as Example 10, but substituting butylamine for dimethylamine, there was prepared 3,4,5-tribromo-N-butyl-α-methylpyrazole-1-acetamide having a melting point at 174° to 175.5° C.

Analysis: Calc'd. for $C_{10}H_{14}Br_3N_3O$: C, 27.80; H, 3.27; N, 9.73; Br, 55.50. Found: C, 27.93; H, 3.54; N, 9.53; Br, 55.75.

EXAMPLE 25

Preparation of 3,4,5-Tribromo-N-tert-butyl-α-methylpyrazole-1-acetamide

Following the same procedure as Example 10, but substituting tert-butylamine for dimethylamine, there was prepared 3,4,5-tribromo-N-tert-butyl-α-methylpyrazole-1-acetamide having a melting point at 200.5° to 201.5° C.

Analysis: Calc'd. for $C_{10}H_{14}Br_3N_3O$: C, 27.80; H, 3.27; N, 9.73; Br, 55.50. Found: C, 27.97; H, 3.53; N, 9.63; Br, 55.87.

EXAMPLE 26

Preparation of 3,4,5-Tribromo-N-cyclohexyl-α-methylpyrazole-1-acetamide

Following the same procedure as Example 10, but substituting cyclohexylamine for dimethylamine, there was prepared 3,4,5-tribromo-N-cyclohexyl-α-methylpyrazole-1-acetamide having a melting point at 234° to 235° C.

Analysis: Calc'd. for $C_{12}H_{16}Br_3N_3O$: C, 31.47; H, 3.52; N, 9.17; Br, 52.34. Found: C, 31.57; H, 3.49; N, 9.23; Br, 52.73.

EXAMPLE 27

Preparation of 3,4,5-Tribromo-N,N-(3-oxapentamethylene)-α-methylpyrazole-1-acetamide Following the same procedure as Example 10, but substituting morpholine for dimethylamine, there was prepared 3,4,5-tribromo-N,N-(3-oxapentamethylene)-α-methylpyrazole-1-acetamide having a melting point at 155.5° to 158.5° C.

Analysis: Calc'd. for $C_{10}H_{12}Br_3N_3O_2$: C, 26.93; H, 2.71; N, 9.42; Br, 53.76. Found: C, 27.09; H, 2.59; N, 9.65; Br, 53.82.

EXAMPLE 28

Preparation of 3,4,5-Tribromo-N-methylpyrazole-1-acetamide

Following the procedure of Example 9, but substituting methylamine for ammonia, there was prepared 3,4,5-tribromo-N-methylpyrazole-1-acetamide having a melting point at 242.5° to 243.5° C.

Analysis: Calc'd. for $C_6H_6Br_3N_3O$: C, 19.17; H, 1.61; N, 11.18; Br, 63.78. Found: C, 19.28; H, 1.43; N, 10,84; Br, 64.28.

EXAMPLE 29

Following the procedure of Example 10, but substituting 3,4,5-tribromopyrazole-1-propionic acid, 3,4,5-tribromopyrazole-1-butyric acid, and 3,4,5-tribromo-α-methylpyrazole-1-propionic acid for 3,4,5-tribromo-α-methylpyrazole-1-acetic acid, there are prepared:

3,4,5-tribromo-N,N-dimethylpyrazole-1-propionamide,
3,4,5-tribromo-N,N-dimethylpyrazole-1-butyramide,
3,4,5-tribromo-N,N,α-trimethylpyrazole-1-propionamide, respectively.

EXAMPLE 30

Preparation of 3,4,5-Tribromo-α-methylpyrazole-1-acetic acid

A quantity (3.04 gm., 0.01 mole) of 3,4,5-tribromopyrazole was dissolved in 70 ml. acetone and 2.76 gm. (0.02 mole) solid anhydrous potassium carbonate was added. The mixture was heated at the reflux temperature with stirring for 10 minutes and, after cooling, 2.0 gm. (0.011 mole) ethyl 2-bromopropionate was added. This reaction mixture was heated at the reflux temperature for 1½ hrs. After cooling, an aqueous solution of sodium hydroxide (0.5 gm. in 90 ml. water) was added. The acetone was distilled off and the remaining aqueous solution was heated at the reflux temperature for 2 hrs. The clear solution thus obtained was cooled and acidified to about pH 2 with 2 N hydrochloric acid. A white precipitate that formed was collected on a filter, washed with water, and dried. There was thus obtained 3.55 gm. (95% yield) of 3,4,5-tribromo-α-methylpyrazole-1-acetic acid having a melting point at 162° to 164° C., identical with the product of Example 5.

Analysis: Calc'd. for $C_6H_5Br_3N_2O_2$: C, 19.12; H, 1.34; N, 7.43; Br, 63.61. Found: C, 19.24; H, 1.55; N, 7.11; Br, 63.71.

EXAMPLE 31

Preparation of 3,4,5-Tribromo-α-ethylpyrazole-1-acetic acid

Following the procedure of Example 30, but substituting ethyl 2-bromobutyrate for ethyl 2-bromopropionate, there was prepared 3,4,5-tribromo-α-ethylpyrazole-1-acetic acid having a melting point at 98° to 100° C.

Analysis: Calc'd. for $C_7H_7Br_3N_2O_2$: C, 21.51; H, 1.81; N, 7.17; Br, 61.33. Found: C, 21.68; H, 1.69; N, 6.86; Br, 61.46.

EXAMPLE 32

Preparation of 3,4,5-Tribromo-α-isopropylpyrazole-1-acetic acid

Following the same procedure as Example 30, but substituting ethyl 2-bromo-3-methylbutyrate for ethyl 2-bromopropionate, there was prepared 3,4,5-tribromo-α-isopropylpyrazole-1-acetic acid having a melting point of 92° to 95° C.

Analysis: Calc'd. for $C_8H_9Br_3N_2O_2$: C, 23.73; H, 2.24; N, 6.92; Br, 59.21. Found: C, 23.82; H, 2.14; N, 6.71; Br, 59.41.

EXAMPLE 33

Preparation of 3,4,5-Tribromo-α-butylpyrazole-1-acetic acid

Following the same procedure as Example 30, but substituting ethyl 2-bromohexanoate for ethyl 2-bromopropionate there was prepared 3,4,5-tribromo-α-butylpyrazole-1-acetic acid having a melting point at 90° to 92° C.

Analysis: Calc'd. for $C_9H_{11}Br_3N_2O_2$: C, 25.80; H, 2.65; N, 6.69; Br, 57.23. Found: C, 25.93; H, 2.79; N, 6.58; Br, 57.31.

EXAMPLE 34

Preparation of Ethyl 3,4,5-Tribromo-α-butylpyrazole-1-acetate

A quantity (30.4 g., 0.1 mole) of 3,4,5-tribromopyrazole was dissolved in 500 ml. acetone and 27.6 g. (0.2 mole) solid anhydrous potassium carbonate was added. The mixture was heated at the reflux temperature with stirring for 10 minutes and after cooling 23.0 g. (0.11 mole) ethyl 2-bromohexanoate was added. This reaction mixture was heated at the reflux temperature for 1½ hrs., cooled, and then filtered. The solids on the filter were washed with acetone and the combined acetone filtrate and acetone washes were evaporated to dryness under reduced pressure. Distillation of the residue yielded ethyl 3,4,5-tribromo-α-butylpyrazole-1-acetate, 41.0 g. (92% yield), having a boiling point at 138° to 140° C. at 0.15 mm. mercury pressure.

Analysis: Calc'd. for $C_{11}H_{15}Br_3N_2O_2$: C, 29.55; H, 3.38; N, 6.27; Br, 53.64. Found: C, 29.93; H, 3.67; N, 6.13; Br, 53.95.

EXAMPLE 35

Preparation of Ethyl 3,4,5-Tribromo-α-ethylpyrazole-1-acetate

Following the same procedure as Example 34, but substituting ethyl 2-bromobutyrate for ethyl 2-bromohexanoate, there was prepared ethyl 3,4,5-tribromo-α-ethylpyrazole-1-acetate.

Analysis: Calc'd. for $C_9H_{11}Br_3N_2O_2$: C, 25.80; H, 2.65; N, 6.69; Br, 57.23. Found: C, 26.35; H, 2.88; N, 6.63; Br, 57.04.

EXAMPLE 36

Preparation of Ethyl 3,4,5-Tribromo-α-isopropylpyrazole-1-acetate

Following the same procedure as Example 34, but substituting ethyl 2-bromo-3-methylbutyrate for ethyl 2-bromohexanoate, there was prepared ethyl 3,4,5-tribromo-α-isopropylpyrazole-1-acetate having a boiling point at 119° C. at 0.05 mm. mercury pressure.

EXAMPLE 37

Preparation of 3,4-Dibromopyrazole-1-ethanol

A solution of 9.7 g. (0.025 mole) ethyl 3,4,5-tribromopyrazole-1-acetate in 125 ml. dry ether was mixed with a suspension of 1.9 g. (0.05 mole) lithium aluminum hydride in 50 ml. dry ether. The reaction mixture was heated at the reflux temperature for two hrs. and then cooled. Ethyl acetate (5 ml.) and then water (30 ml.) were added and after settling the ether portion was decanted. The ether solution was washed with two 40-ml. portions of water and dried over anhydrous sodium sulfate. After removing the ether by evaporation, the oily residue was treated with decolorizing charcoal and crystallized from a mixture of ethyl ether and petroleum ether (boiling at the temperature range 30° C. to 60° C.). There was thus obtained 6.5 gms. (75% yield) of 3,4-dibromopyrazole-1-ethanol having a melting point of 64° to 66° C.

Analysis: Calc'd. for $C_5H_6Br_2N_2O$: C, 22.24; H, 2.24; N, 10.37; Br, 59.20. Found: C, 22.63; H, 2.45; N, 10.52; Br, 59.01.

EXAMPLE 38

Preparation of 3,4-Dibromo-β-methylpyrazole-1-ethanol

Following the procedure of Example 37, but substituting ethyl 3,4,5-tribromo-α-methylpyrazole-1-acetate for ethyl 3,4,5-tribromopyrazole-1-acetate, there was prepared 3,4-dibromo-β-methylpyrazole-1-ethanol having a melting point at 83.5° to 84.5° C.

Analysis: Calc'd. for $C_6H_8Br_2N_2O$: C, 25.38; H, 2.84; N, 9.87; Br, 56.28. Found: C, 25.53; H, 2.92; N, 9.65; Br, 55.85.

EXAMPLE 39

Preparation of 3,4-Dibromo-α-methylpyrazole-1-acetic acid

To a suspension of 3,4-dibromo-β-methylpyrazole-1-ethanol (2.8 g., 0.01 mole) prepared in Example 38, above, in sodium hydroxide (0.3 g., 0.0075 mole) and water (3.0 ml.), a solution of potassium permanganate (3.4 g., 0.0215 mole) in water (30 ml.) was added over a period of 20 minutes. A further 30 ml. of water was added and the reaction mixture was stirred at about 25° C. for 4 hours, followed by acidification with 6N sulfuric acid and addition of sodium bisulfite until all the precipitated manganese dioxide went into solution. The aqueous solution was extracted with three 50-ml. portions of ether and the combined ether extracts were washed with water and dried over anhydrous sodium sulfate. Evaporation of the ether under reduced pressure followed by chromatography on silica gel using the solvent system benzene, 85:chloroform, 5:glacial acetic acid, 10 (by volume) gave a solid which on recrystallization from acetone-hexane gave 3,4-dibromo-α-methylpyrazole-1-acetic acid having a melting point at 124.5° to 126° C.

Analysis: Calc'd. for $C_6H_6Br_2N_2O_2$: C, 24.18; H, 2.03; N, 9.40; Br, 53.64. Found: C, 23.98; H, 2.06; N, 9.63; Br, 53.97.

EXAMPLE 39A

Preparation of 3,4-dibromo-N,N,α-trimethylpyrazole-1-acetamide

Following the same procedure as described in Example 10, but substituting the 3,4-dibromo-α-methylpyrazole-1-acetic acid prepared in Example 39, above, for 3,4,5-tribromo-α-methylpyrazole-1-acetic acid, there was prepared 3,4-dibromo-N,N,α-trimethylpyrazole-1-acetamide having a melting point at 139° to 141° C.

Analysis: Calc'd. for $C_8H_{11}Br_2N_3O$: C, 29.56; H, 3.41; N, 12.93. Found: C, 29.83; H, 3.49; N, 13.01.

EXAMPLE 39B

Preparation of Ethyl
3,5-dibromo-α-methylpyrazole-1-acetate

Following the same procedure as described in Example 34, but substituting 3,5-dibromopyrazole, [Synthesized by the method of Hutell and Schon, *Ann.*, 625, 55 (1959)] for 3,4,5-tribromopyrazole and ethyl-2-bromopropionate for ethyl-2-bromohexanoate there was prepared ethyl 3,5-dibromo-α-methylpyrazole-1-acetate having a boiling point at 118° C. and 0.04 mm. mercury pressure.

Analysis: Calc'd. for $C_8H_{10}Br_2N_2O_2$: C, 29.47; H, 3.09; N, 8.59; Br, 49.02. Found: C, 29.78; H, 3.59; N, 8.66; Br, 48.69.

EXAMPLE 39C

Preparation of ethyl-3,5-dibromopyrazole-1-acetate

Following the same procedure as described in Example 34, but substituting 3,5-dibromopyrazole for 3,4,5-tribromopyrazole and ethyl bromoacetate for ethyl 2-bromohexanoate there was prepared ethyl-3,5-dibromopyrazole-1-acetate in a yield of 90% having a melting point at 52° to 53° C.

Analysis: Calc'd. for $C_7H_8Br_2N_2O_2$: C, 26.95; H, 2.58; N, 8.98. Found: C, 27.26; H, 2.58; N, 9.08.

EXAMPLE 39D

Preparation of 3,5-Dibromo-α-methylpyrazole-1-acetic acid

Following the procedure of Example 30, but substituting 3,5-dibromopyrazole for 3,4,5-tribromopyrazole there was prepared 3,5-dibromo-α-methylpyrazole-1-acetic acid having a melting point at 126.5° to 127.5° C.

Analysis: Calc'd. for $C_6H_6Br_2N_2O_2$: C, 24.18; H, 2.03; N, 9.40; Br, 53.64. Found: C, 24.09; H, 1.99; N, 9.50; Br, 53.47.

EXAMPLE 39E

Preparation of 3,5-Dibromopyrazole-1-acetic acid

Following the procedure of Example 30, but substituting 3,5-dibromopyrazole for 3,4,5-tribromopyrazole and ethyl bromoacetate for ethyl-2-bromopropionate there was prepared 3,5-dibromopyrazole-1-acetic acid in a yield of 72% having a melting point at 193° to 195° C.

Analysis: Calc'd. for $C_5H_4Br_2N_2O_2$: C, 21.15; H, 1.42; N, 9.87. Found: C, 21.26; H, 1.80; N, 9.79.

EXAMPLE 39F

Preparation of
3,5-Dibromo-N,N,α-trimethylpyrazole-1-acetamide

Following the same procedure as described in Example 10, but substituting 3,5-dibromo-α-methylpyrazole-1-acetic acid (prepared in Example 39E, above) for 3,4,5-tribromo-α-methylpyrazole-1-acetic acid, there was prepared 3,5-dibromo-N,N,α-trimethylpyrazole-1-acetamide in a yield of 85% having a melting point at 139° to 141° C.

Analysis: Calc'd. for $C_8H_{11}Br_2N_3O$: C, 29.56; H, 3.41; N, 12.93. Found: C, 29.48; H, 3.11; N, 12.90.

EXAMPLE 40

Preparation of 3,4,5-Tribromopyrazole-1-ethanol acetate (ester)

A quantity (3.04 g., 0.01 mole) of 3,4,5-tribromopyrazole was dissolved in 70 ml. acetone and 2.76 g. (0.02 mole) solid anhydrous potassium carbonate was added. The mixture was heated at the reflux temperature with stirring for 10 minutes and after cooling, 1.85 g. (0.011 mole) of 2-bromoethyl acetate was added. This reaction mixture was heated at the reflux temperature for 12 hrs. cooled, filtered, and the acetone removed under reduced pressure. The resultant oil consisted of a mixture of the desired acetate and the corresponding alcohol. The mixture was dissolved in pyridine (15 ml.) and treated with acetic anhydride (3.06 g., 0.03 mole) at 0° C. This reaction mixture was kept at about 25° C. overnight, and then poured into 200 ml. of ice water. The precipitate that formed was collected on a filter, and washed with water. After drying and recrystallizing from hexane there was obtained 3,4,5-tribromopyrazole-1-ethanol acetate (ester) having a melting point at 64° to 67° C.

Analysis: Calc'd. for $C_7H_7Br_3N_2O_2$: C, 21.51; H, 1.81; N, 7.17; Br, 61.33. Found: C, 21.88; H, 1.95; N, 7.14; Br, 61.42.

EXAMPLE 41

Preparation of 3,4,5-Tribromopyrazole-1-ethanol

A quantity of the acetone-free oil obtained in an identical manner to the procedure described in Example 40, above, was treated with 20 ml. 0.5N ethanolic sodium hydroxide, and heated at the reflux temperature for 1.5 hrs. The solvent was removed by evaporation under reduced pressure, and the residue thus obtained was dissolved in ether. The ether solution was washed with water and dried, and the ether was removed by evaporation under reduced pressure. There was thus obtained 3,4,5-tribromopyrazole-1-ethanol having a melting point at 68° to 70° C.

Analysis: Calc'd. for $C_5H_5Br_3N_2O$: C, 17.21; H, 1.44; N, 8.03; Br, 68.72. Found: C, 17.26; H, 1.50; N, 8.05; Br, 69.17.

EXAMPLE 42

Preparation of
3,4,5-Tribromo-3',4'-dichloro-α-methylpyrazole-1-acetanilide

A mixture consisting of 10 gm. (0.0266 mole) 3,4,5-tribromo-α-methylpyrazole-1-acetic acid (prepared as in Example 5) and 10 ml. thionyl chloride was heated at the reflux temperature for 3½ hrs. After removing any unreacted thionyl chloride by evaporation under reduced pressure, the unpurified 3,4,5-tribromo-α-methylpyrazole-1-acetyl chloride was dissolved in 25 ml. benzene. The benzene solution was added dropwise with stirring to a mixture consisting of 4.3 gm. (0.0266 mole) 3,4-dichloroaniline, 3.0 gm. (0.03 mole) triethylamine, and 100 ml. dry benzene. This reaction mixture was held at about 25° C. for ½ hr. with continuous stirring. The reaction mixture was then heated at the reflux temperature for another ½ hr. After cooling a precipitate that had formed was collected on a filter, washed with water and recrystallized from 95% ethanol. There was thus obtained 10 gm. of 3,4,5-tribromo-3',4'- dichloro-α-methylpyrazole-1-acetanilide having a melting point at 217° to 218° C.

Analysis: Calc'd. for $C_{12}H_8Br_3Cl_2N_3O$: C, 27.67; H, 1.55; N, 8.07. Found: C, 27.84; H, 1.73; N, 7.91.

Following the same procedure, but substituting N-methylethylamine, N-methylbenzylamine, N-methylaniline, N-allylaniline, N-methyl-p-toluidine, N-butyl-4-tert-butylaniline, N-methyl-2,5-dichloroaniline, 2,6-dinitro-4-trifluoromethylaniline, 4-trifluoromethylaniline, 2,6-dinitro-p-toluidine, 2,6-dinitroaniline, 4-chloro-2,6-dinitroaniline, 2-methylpyrrolidine, 2-sec-butylpyrrolidine, 3,4-dimethylpyrrolidine, 3,4-diethylpiperidine, 2-ethyl-5-methylmorpholine, 2,6-dimethylmorpholine, 3-methylmorpholine, 2,3,5,6-tetramethylthiamorpholine, 4-butylpiperazine, 2,2,4,5,5-pentamethylpiperazine, hexamethyleneimine, 2-ethylhexamethyleneimine, and 3-heptylhexamethyleneimine for 3,4-dichloroaniline, there are prepared the corresponding:

3,4,5-tribromo-N-ethyl-N,α-dimethylpyrazole-1-acetamide,
3,4,5-tribromo-N-benzyl-N,α-dimethylpyrazole-1-acetamide,
3,4,5-tribromo-N,α-dimethylpyrazole-1-acetanilide,
3,4,5-tribromo-N-allyl-α-methylpyrazole-1-acetanilide,
3,4,5-tribromo-N,α-dimethyl-4'-methylpyrazole-1-acetanilide,
3,4,5-tribromo-N-butyl-4'-tert-butyl-α-methylpyrazole-1-acetanilide,
3,4,5-tribromo-2',5'-dichloro-N,α-dimethylpyrazole-1-acetanilide,
3,4,5-tribromo-2',6'-dinitro-α-methyl-4'-trifluoromethylpyrazole-1-acetanilide,
3,4,5-tribromo-α-methyl-4'-trifluoromethylpyrazole-1-acetanilide,
3,4,5-tribromo-α,4'-dimethyl-2',6'-dinitropyrazole-1-acetanilide,
3,4,5-tribromo-2',6'-dinitro-α-methylpyrazole-1-acetanilide,
3,4,5-tribromo-4'-chloro-2',6'-dinitro-α-methyl-pyrazole-1-acetanilide,
3,4,5-tribromo-α-methyl-N,N-(1-methyltetramethylene)pyrazole-1-acetamide,
3,4,5-tribromo-α-methyl-N,N-(1-sec-butyltetramethylene)pyrazole-1-acetamide,
3,4,5-tribromo-α-methyl-N,N-(2,3-dimethyltetramethylene)pyrazole-1-acetamide,
3,4,5-tribromo-α-methyl-N,N-(2,3-diethylpentamethylene)pyrazole-1-acetamide,
3,4,5-tribromo-α-methyl-N,N-(4-ethyl-1-methyl-3-oxapentamethylene)pyrazole-1-acetamide,
3,4,5-tribromo-α-methyl-N,N-(2,4-dimethyl-3-oxapentamethylene)pyrazole-1-acetamide,
3,4,5-tribromo-α-methyl-N,N-(1-methyl-3-oxapentamethylene)pyrazole-1-acetamide,
3,4,5-tribromo-α-methyl-N,N-(1,2,4,5-tetramethyl-3-thiapentamethylene)pyrazole-1-acetamide,
3,4,5-tribromo-α-methyl-N,N-(3-butyl-3-azapentamethylene)pyrazole-1-acetamide,
3,4,5-tribromo-α-methyl-N,N-(1,1,3,4,4-pentamethyl-3-azapentamethylene)pyrazole-1-acetamide,
3,4,5-tribromo-α-methyl-N,N-(hexamethylene)-pyrazole-1-acetamide,
3,4,5-tribromo-α-methyl-N,N-(1-ethylhexamethylene)-pyrazole-1-acetamide, and
3,4,5-tribromo-α-methyl-N,N-(2-heptylhexamethylene)pyrazole-1-acetamide, respectively.

EXAMPLE 43

Preparation of 3,4,5-Tribromo-3',4'-dichloropyrazole-1-acetanilide

Following the procedure of Example 42, but substituting 3,4,5-tribromopyrazole-1-acetic acid for 3,4,5-tribromo-α-methylpyrazole-1-acetic acid, there was prepared 3,4,5-tribromo-3',4'-dichloropyrazole-1-acetanilide having a melting point at 232° to 232.5° C.

Analysis: Calc'd. for $C_{11}H_6Br_3Cl_2N_3O$: C, 26.07; H, 1.19; N, 8.29. Found: C, 26.13; H, 0.94; N, 8.43.

EXAMPLE 44

Preparation of 3,4,5-Tribromopyrazole-1-acetonitrile

To a suspension of sodium hydride (2.2 gm. of a 60.6% dispersion in mineral oil, containing 0.055 mole of sodium hydride) in 60 ml. toluene was added a solution of 3,4,5-tribromopyrazole (15.2 gm., 0.05 mole) in 400 ml. hot toluene, followed by the dropwise addition of chloroacetonitrile (4.2 gm., 0.055 mole). The mixture was heated at the reflux temperature for 3 hrs. and then allowed to stand at about 25° C. for 18 hrs. Water (50 ml.) was added. The toluene layer was separated, washed with two 80-ml. portions of water, and dried with anhydrous sodium sulfate. Removal of the toluene gave 14.4 g. of 3,4,5-tribromopyrazole-1-acetonitrile as a white solid which was recrystallized from a mixture of ether and technical hexane.

Analysis: Calc'd. for $C_5H_2Br_3N_3$: C, 17.46; H, 0.59; N, 12.22; Br, 69.73. Found: C, 17.51; H, 0.84; N, 12.09; Br, 69.69.

Following the same procedure, but substituting 3-chloropropionitrile, 3-chloro-2-methylpropionitrile, 3-bromovaleronitrile, and 4-chlorobutyronitrile for chloroacetonitrile, there are prepared 3,4,5-tribromopyrazole-1-propionitrile, 3,4,5-tribromo-α-methylpyrazole-1-propionitrile, 3,4,5-tribromo-β-ethylpyrazole-1-propionitrile, and 3,4,5-tribromopyrazole-1-butyronitrile, respectively.

EXAMPLE 45

Preparation of 3,4,5-Tribromo-α-methylpyrazole-1-acetonitrile

Following the procedure of Example 44, but substituting 2-bromopropionitrile for chloroacetonitrile, there was prepared 3,4,5-tribromo-α-methylpyrazole-1-acetonitrile having a melting point at 100° to 102° C.

Analysis: Calc'd. for $C_6H_4Br_3N_3$: C, 20.14; H, 1.13; N, 11.74; Br, 66.99. Found: C, 20.33; H, 1.10; N, 11.66; Br, 66.96.

The new 1-(substituted-hydrocarbyl)-di- and trihalopyrazoles of this invention (compounds of Formula I) have been found to be active as herbicides and plant growth regulators. The new compounds can be used to prevent damage to field crops due to weed competition, and they can be used to prevent unsightly and deleterious growths of weeds on home lawns, golf courses, cemeteries, railroad rights-of-way, and parks.

Compounds of this invention have been found to be highly active against both broadleaf and grassy weeds, with some variations between one compound and another within the series. Illustratively, 3,4,5-tribromo-N,N,α-trimethylpyrazole-1-acetamide and 3,4,5-tribromo-α-methylpyrazole-1-acetic acid are especially active against various weeds, e.g., crabgrass (*Digitaria sanguinalis L.*), yellow foxtail (*Setaria glauca L.*), wild oats (*Avena fatua L.*), bindweed (*Convolvulus arvensis L.*), Johnson grass (*Sorghum halepense L.*), buckhorn plantain (*Plantago lanceolata L.*), curly dock (*Rumex crispus L.*), wild mustard (*Brassica kaber DG.*), purslane (*Portulaca oleracea L.*), and barnyard-grass (*Echinochloa crusgalli L.*).

Illustratively, control and significant growth retardation of the foregoing weed species has been achieved using the named compounds and other specific compounds of this invention at rates of from 1 to 12.5 lbs. per acre. Depending upon the kinds of weeds to be controlled, the stage of weed development, the degree of infestation, and the presence or absence of aesthetic or crop plants, the compounds of this invention can be applied to soil, germinating weed seeds, weed seedlings, plant growth media, growing plants, or any other selected situs for control of weeds at rates ranging from about ¼ to ½ lb. per acre up to about 50 lbs. per acre. Ordinarily, the situs will be soil, but this term is used in the broad sense — anywhere where weed growth might be a problem, e.g., gravel driveways, railroad beds, flat built-up roofs, ponds, lakes, streams, and canals. Aquatic applications effectively use about 2 to about 10,000 or more, parts per million (ppm), by weight.

The new 1-(substituted-hydrocarbyl)-di- or trihalopyrazoles of Formula I can be applied to a situs in a dispersible pure form, but dispersible formulations for herbicidal use are preferred. The dispersible formulations of this invention comprise a 1-(substituted-hydrocarbyl)-di- or trihalopyrazole in a homogeneous, dispersible form with a homogeneous dispersible carrier. Adjuvants such as surfactants, humectants, dispersants, adhesive or sticking agents, corrosion inhibitors, and anti-foaming agents can be included.

A homogeneous dispersible carrier comprehends a particulate solid carrier or a liquid carrier diluent. The compound can be dispersed in a liquid carrier diluent as a solute or as finely divided particles (suspension).

The term "dispersible", as used in this specification and in the claims, means matter in a liquid or particulate state such that it can be evenly distributed over a given area or metered into a body of water. A "liquid" state includes true solutions as well as dispersions of particulate solids in a liquid. Emulsions of one liquid in another, e.g., oil-in-water, are also contemplated. The active compound can be in either the dispersed phase, the continuous phase, or partitioned between them both. In general, the active compound will be preponderantly in the dispersed phase when emulsions are used. A "particulate" state includes the general concept of finely divided separate particles, and granular particles as large as 10 mesh (U.S.) or even somewhat larger when appropriate herbicidal practice indicates an advantage in using larger granules.

The granular particles could be included in what is termed an "interstitial" state, which contemplates the deposition or entrapment of the active compound within the interstices of a porous body. For example, the compounds can be mixed with an elastomer, e.g., natural rubber, chloroprene, butyl rubber, polyether and polyester urethanes and the like, which may be further processed according to conventional techniques in the elastomeric art. The latter elastomeric matrices as well as conventional granules provide a slow, sustained release of the active herbicide so that herbicidal concentrations of the active compound can be obtained over a prolonged interval for the control of weeds.

Illustrative of the adjuvants named above, humectants include glycerol, diethylene glycol, solubilized lignins (such as calcium ligninsulfonate), and the like. Dispersants include methyl cellulose, polyvinyl alcohol, sodium ligninsulfonate, and the like. Adhesive or sticking agents include vegetable oils, naturally occurring gums, casein, and the like. A suitable corrosion inhibitor is epichlorohydrin, and a suitable anti-foaming agent is stearic acid.

Representative surfactants include alkyl sulfates and sulfonates, alkyl aryl sulfonates, sulfosuccinate esters, polyoxyethylene sulfates, polyoxyethylenesorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants includes blends of sulfonated oils and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul N₄S). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powder formulations can be prepared with a mixture of surfactants of the types indicated if desired.

The concentration of the active compound, a new 1-(substituted-hydrocarbyl)-di- or trihalopyrazole according to this invention, in the new herbicidal formulations of this invention is not usually a critical, limiting factor in achieving a desired herbicidal effect. The most important factor is how much compound is applied to an area of weeds to be controlled. It is readily apparent that one can apply a large amount of a formulation having a low concentration of active compound or a relatively small amount of a formulation having a high concentration. Whether a low or high concentration should be used depends upon the mode of application, the amount and kinds of vegetation, and the thoroughness of coverage desired. The total amount to be applied depends upon the kinds of weeds and crop, if any, the severity of infestation, the stage of plant development, and the season of the year.

Representative homogeneous dispersible formulations according to this invention include sprays, dusts, and granular formulations. Spray formulations are preferred for foliar applications and for uniformly controlled applications to a soil. Granular formulations are usually applied in bands spanning the seeded row, although broadcast distribution is advantageous when soil incorporation is practiced and a prolonged effect is desired.

The spray formulations in accordance with the invention can be aqueous solutions, aqueous suspensions, water-in-oil emulsions, oil-in-water emulsions, and oil solutions. The spray formulations will conveniently comprise from about 0.1% or lower to about 50% by weight or even higher, a volume of spray being applied so that a herbicidally effective amount of 1-(substituted-hydrocarbyl)-di- or trihalopyrazole is distributed over the treated area. Sprays containing about 0.25 ounce to about 16 lbs. of 1-(substituted-hydrocarbyl)-di- or trihalopyrazole in a 20 gal. to 40 gal. volume are applied to foliage or soil for effective herbicidal action.

Concentrates for preparing spray formulations are advantageously prepared by dissolving the active compounds of the invention in a solvent, or by dispersing the active compounds in a dispersible solid or liquid diluent. Illustratively, the herbicidally active 1-(substituted-hydrocarbyl)-di- or trihalopyrazoles of this invention are dissolved or dispersed in water or a suitable water-miscible or water-immiscible inert organic liquid. Representative water-miscible organic liquids include acetone, methyl ethyl ketone, dimethylformamide, alcohols, monoalkyl ethers of ethylene glycol, ethyl acetate, and the like. Representative substantially water-immiscible organic liquids (i.e., a solvent carrier which is soluble in water to the extent of less than 2.5% by volume at temperatures of the order of 20° to 30° C.) for preparing emulsifiable concentrates include petroleum oils, distillates, toluene, xylene, cumene, and like aromatic hydrocarbons, isoparaffin oil, mineral oil, and the like.

Advantageously, the concentration of active ingredient in the emulsifiable concentrates (with or without surfactant) can range from about 5% to about 50% by weight, preferably from about 10% to about 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm (parts per million) of active ingredient. In the same manner, more concentrated solutions of active ingredient can be prepared.

Dust formulations in accordance with the invention are readily prepared by dispersing the active compound in a dispersible solid by grinding a mixture of the compound and a pulverulent solid carrier in the presence of each other. Grinding is conveniently accomplished in a ball mill, a hammermill, or by air-blast micronization. These dust compositions can also be prepared by dissolving the 1-(substituted-hydrocarbyl)-di- or trihalopyrazole in a volatile solvent such as methylene chloride, mixing the solution with a pulverulent solid carrier, evaporating the solvent, and pulverizing the impregnated carrier. A suitable ultimate particle size is less than 60 microns. Preferably, 95% of the particles are less than 50 microns, and about 75% are 5 to 20 microns. Dusts of this degree of comminution are conveniently free-flowing. Dusts are particularly adapted for air-borne application over ponds, lakes, marshes, swamps, swales, and potholes.

Representative suitable pulverulent solid carriers include the natural clays such as China, Georgia, Barden, attapulgus, kaolin, and bentonite clays; minerals in their natural forms as they are obtained from the earth such as talc, pyrophyllite, quartz, diatomaceous earth, fuller's earth, chalk, rock phosphates and sulfates, calcium carbonates, sulfur, silica and silicates; chemically modified minerals such as washed bentonite, precipitated calcium phosphate, precipitated calcium carbonate, precipitated calcium silicate, synthetic magnesium silicate, and colloidal silica; and organic flours such as wood, walnut shell, soybean, cottonseed, and tobacco flours, and free-flowing, hydrophobic starches.

The proportions of pulverulent carrier and 1-(substituted-hydrocarbyl)-di- or trihalopyrazole can vary over a wide range depending upon the plants to be controlled, rates of application according to equipment available, and the conditions of treatment. In general, dust formulations can contain up to about 90% (on a weight basis) of the active ingredient. Dusts having as little as 0.001% of the active ingredient can be used, but a generally preferred proportion is from about 0.50% to about 20% of active ingredient.

Advantageously, a dust formulation as described above includes a surfactant, because about 0.1% to about 12% of a surfactant promotes dispersibility of a dust in water and facilitates formulation of aqueous sprays or dispersibility of a dust formulation applied directly to water surfaces or aquatic weeds. Dust formulations comprising a surfactant are known as dispersible or wettable powders. As indicated, dispersible or wettable powders can be admixed with water to obtain any desired concentration of active ingredient. The dispersible or wettable powders can conveniently comprise from about 10% to about 90% active ingredient, preferably about 30% to about 80%.

A suitable dispersible powder formulation is obtained by blending and milling 327 lbs. of Georgia Clay, 4.5 lbs. of isooctylphenoxy polyethoxy ethanol (Triton X-100) as a wetting agent, 9 lbs. of a polymerized sodium salt of substituted benzcid long-chain sulfonic acid (Daxad 27) as a dispersing agent, and 113 lbs. of the active ingredient. The resulting formulation has the following percentage composition (parts herein are by weight unless otherwise specified):

| | |
|---|---|
| Active ingredient | 25% |
| Isooctylphenoxy polyethoxy ethanol | 1% |
| Polymerized sodium salt of substituted benzoid long-chain sulfonic acid | 2% |
| Georgia Clay | 72% |

This formulation, when dispersed in water at the rate of 10 lbs. per 100 gals., gives a spray formulation containing about 0.3% (3000 ppm) active ingredient which can be applied to weeds at the rate of 40 gals. per acre to give a total application of active ingredient of 1 lb. per acre.

The new 1-(substituted-hydrocarbyl)-di- and trihalopyrazoles of this invention, more particularly, 3,4,5-tribromo-α-methylpyrazole-1-acetic acid, possess advantageous plant growth regulatory activity and they modify the normal apical dominance and produce symptoms of epinasty when applied to growing plants. They can be used to promote lateral bud growth and increased numbers of fruiting bodies.

Further in accordance with this invention, certain formulations of the new 1-(substituted-hydrocarbyl)-di- and trihalopyrazoles of this invention with oil are particularly efficacious, and herbicidal action of the compound is improved. Any petroleum oil can be used so long as it is not so viscous as to be too difficult to disperse. A non-phytotoxic oil is satisfactory.

Advantageously, a 50% wettable powder of the herbicidal active ingredient is mixed with about 38 gals. water and 2 gals. oil for spray application. Alternatively, about 2 gals. oil and a 50% wettable powder are premixed and then dispersed in about 38 gals. water for spray application. In field tests, oil formulations of the foregoing type have given improved herbicidal action.

We claim:

1. New 1-(substituted-hydrocarbyl)-di- and trihalopyrazoles of the formula:

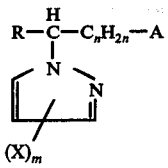

wherein "n" is an integer 0, 1, 2, or 3; "X" is a bromine on chlorine atom; "m" is the integer 2 or 3, the bromine or chlorine atoms being selected independently; "R" is hydrogen, alkyl of from 1 to 10 carbon atoms, inclusive, or alkenyl of from 2 to 10 carbon atoms, inclusive, the sum of the carbon atoms in the group

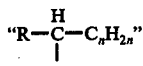

being not more than 11; and "A" is the carboxyl group and alkali metal, alkaline earth metal, ammonium and amine salts thereof, a hydroxymethyl lower-alkanoate group in which the lower-alkyl moiety is of from 1 to 8 carbon atoms, inclusive, a carboxylic lower-alkyl ester group wherein "lower-alkyl" is of from 1 to 8 carbon atoms, inclusive.

2. Compounds according to claim 1 wherein "X" is bromine.

3. Compounds according to claim 2 wherein "m" is 2.

4. Dibromopyrazoles according to claim 3 wherein "n" is 0 and "A" is a carboxylic group.

5. The new compound according to claim 4, 3,5-dibromo-α-methylpyrazole-1-acetic acid.

6. The new compound according to claim 4, 3,4-dibromo-β-methylpyrazole-1-acetic acid.

7. The new compound according to claim 4, 3,5-dibromopyrazole-1-acetic acid.

8. Dibromopyrazoles according to claim 3 wherein "n" is 0 and "A" is a carboxylic lower-alkyl ester group.

9. The new compound according to claim 8, ethyl 3,5-dibromopyrazole-1-acetate.

10. The new compound according to claim 8, ethyl 3,5-dibromo-α-methylpyrazole-1-acetate.

11. Compounds according to claim 2 wherein "m" is 3.

12. Tribromopyrazoles according to claim 11 wherein "A" is the carboxyl group.

13. Tribromopyrazoles according to claim 12 wherein "n" is 0.

14. The new compound according to claim 13, 3,4,5-tribromopyrazole-1-acetic acid.

15. The new compound according to claim 13, 3,4,5-tribromo-α-ethylpyrazole-1-acetic acid.

16. The new compound according to claim 13, 3,4,5-tribromo-α-methylpyrazole-1-acetic acid.

17. The new compound according to claim 13, 3,4,5-tribromo-α-isopropylpyrazole-1-acetic acid.

18. The new compound according to claim 13, 3,4,5-tribromo-α-butylpyrazole-1-acetic acid.

19. The new compound according to claim 12, 3,4,5-tribromopyrazole-1-propionic acid.

20. The new compound according to claim 12, 3,4,5-tribromopyrazole-1-butyric acid.

21. Tribromopyrazoles according to claim 11 wherein "n" is 0 and "A" is a carboxylic ester group.

22. The new compound according to claim 21, ethyl 3,4,5-tribromopyrazole-1-acetate.

23. The new compound according to claim 21, ethyl 3,4,5-tribromo-α-methylpyrazole-1-acetate.

24. The new compound according to claim 21, ethyl 3,4,5-tribromo-α-butylpyrazole-1-acetate.

25. The new compound according to claim 21, ethyl 3,4,5-tribromo-α-ethylpyrazole-1-acetate.

26. The new compound according to claim 21, ethyl 3,4,5-tribromo-α-isopropylpyrazole-1-acetate.

27. Tribromopyrazoles according to claim 11 wherein "A" is an hydroxymethyl lower-alkanoate group.

28. The new compound according to claim 27, 3,4,5-tribromopyrazole-1-ethanol acetate (ester).

29. The method of controlling weeds which comprises applying to germinating weed seeds, weed seedlings and other situs of weeds a dispersible inert carrier and a herbicidal amount of a 1-(substituted-hydrocarbyl)-di- or trihalopyrazole of the formula:

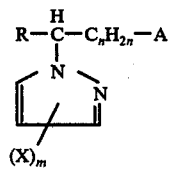

wherein "n" is an integer 0, 1, 2, or 3; "X" is a bromine or a chlorine atom; "m" is the integer 2 or 3, the bromine and chlorine atoms being selected independently; "R" is hydrogen, alkyl of from 1 to 10 carbon atoms, inclusive, or alkenyl of from 2 to 10 carbon atoms, inclusive, the sum of the carbon atoms in the group

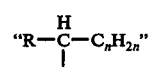

being not more than 11; and "A" is the carboxyl group and alkali metal, alkaline earth metal, ammonium and amine salts thereof, a hydroxymethyl lower-alkanoate group in which the lower-alkyl moiety is of from 1 to 8 carbon atoms, inclusive, and a carboxylic lower-alkyl ester group wherein "lower-alkyl" is of from 1 to 8 carbon atoms, inclusive.

30. The method according to claim 29 wherein the compound is a carboxylic acid.

31. The method according to claim 30 wherein the compound is 3,4,5-tribromopyrazole-1-acetic acid.

32. The method according to claim 30 wherein the compound is 3,4,5-tribromo-α-methylpyrazole-1-acetic acid.

33. Formulations for weed control comprising a dispersible inert carrier and a herbicidal amount of a 1-(substituted-hydrocarbyl)-di- or trihalopyrazole of the formula

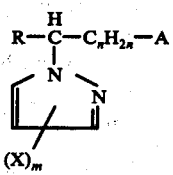

wherein "$n$" is an integer 0, 1, 2, or 3; "$X$" is a bromine or chlorine atom; "$m$" is the integer 2 or 3, the bromine and chlorine atoms being selected independently; "$R$" is hydrogen, alkyl of from 1 to 10 carbon atoms, inclusive, or alkenyl of from 2 to 10 carbon atoms, inclusive, the sum of the carbon atoms in the group

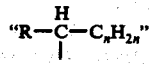

being not more than 11; and "$A$" is the carboxyl group and alkali metal, alkaline earth metal, ammonium and amine salts thereof, a hydroxymethyl lower-alkanoate group in which the lower-alkyl moiety is of from 1 to 8 carbon atoms, inclusive, a carboxylic lower-alkyl ester group wherein "lower-alkyl" is of from 1 to 8 carbon atoms, inclusive.

34. Formulations according to claim 33 wherein the compound is a carboxylic acid.

35. Formulation according to claim 34 wherein the compound is 3,4,5-tribromopyrazole-1-acetic acid.

36. Formulation according to claim 34 wherein the compound is 3,4,5-tribromo-α-methylpyrazole-1-acetic acid.

* * * * *